US012740805B2

(12) United States Patent
Rizk et al.

(10) Patent No.: US 12,740,805 B2
(45) Date of Patent: Sep. 22, 2026

(54) SYSTEMS AND METHODS FOR DRAINING CEREBROSPINAL FLUID

(71) Applicant: THE PENN STATE RESEARCH FOUNDATION, University Park, PA (US)

(72) Inventors: Elias Rizk, University Park, PA (US); Sprague W. Hazard, III, University Park, PA (US)

(73) Assignee: THE PENN STATE RESEARCH FOUNDATION, University Park (PA)

( * ) Notice: Subject to any disclaimer, the term of this patent is extended or adjusted under 35 U.S.C. 154(b) by 0 days.

(21) Appl. No.: 19/017,175

(22) Filed: Jan. 10, 2025

(65) Prior Publication Data

US 2025/0143744 A1 May 8, 2025

Related U.S. Application Data

(63) Continuation of application No. 18/841,260, filed as application No. PCT/US2023/062813 on Feb. 17, 2023.

(Continued)

(51) Int. Cl.
*A61B 17/34* (2006.01)
*A61B 17/12* (2006.01)
(Continued)

(52) U.S. Cl.
CPC ...... *A61B 17/3415* (2013.01); *A61B 17/1204* (2013.01); *A61B 17/12109* (2013.01);
(Continued)

(58) Field of Classification Search
CPC ........... A61B 17/3415; A61B 17/3472; A61M 60/126; A61M 60/157; A61M 60/161; A61M 60/47
See application file for complete search history.

(56) References Cited

U.S. PATENT DOCUMENTS 3,957,050 A 5/1976 Hines
4,362,161 A 12/1982 Reimels
(Continued)

FOREIGN PATENT DOCUMENTS

WO 1996018431 A1 6/1996
WO 2000/061017 A1 10/2000
(Continued)

OTHER PUBLICATIONS

International Search Report of related PCT/US2023/062813, mailed on Sep. 7, 2023, 11 pages.
(Continued)

*Primary Examiner* — Bhisma Mehta
*Assistant Examiner* — Fatimata Sahra Diop
(74) *Attorney, Agent, or Firm* — Quarles & Brady LLP

(57) ABSTRACT

An implant system can include a body defining a first end and a second end opposite the first end. The body can include an exterior surface including threads. The implant system can include a needle coupled to the body and extending past the second end of the body. The body can be configured to be driven into an opening in a bone to place the implant into the bone, thereby securing the implant to the bone. The body can be configured to be driven into the opening in the bone such that the needle pierces a tissue adjacent to the bone, thereby placing an end of the needle into an anatomical cavity.

14 Claims, 13 Drawing Sheets

Related U.S. Application Data

(60) Provisional application No. 63/314,232, filed on Feb. 25, 2022.

(51) Int. Cl.
*A61M 27/00* (2006.01)
*A61B 17/00* (2006.01)

(52) U.S. Cl.
CPC .... *A61B 17/12159* (2013.01); *A61B 17/3468* (2013.01); *A61B 17/3472* (2013.01); *A61M 27/006* (2013.01); *A61B 2017/00407* (2013.01)

(56) References Cited

U.S. PATENT DOCUMENTS

| | | | | |
|---|---|---|---|---|
| 4,600,006 | A | 7/1986 | Baker | |
| 4,803,982 | A | 2/1989 | Baker | |
| 5,267,964 | A * | 12/1993 | Karg | A61M 5/1424 604/141 |
| 5,352,207 | A | 10/1994 | Nussbaum | |
| 5,372,583 | A * | 12/1994 | Roberts | A61M 25/06 604/506 |
| 2003/0045936 | A1* | 3/2003 | Angelucci | A61B 17/7059 623/17.11 |
| 2005/0119603 | A1 | 6/2005 | Kuhlman et al. | |
| 2006/0224101 | A1* | 10/2006 | Glenn | A61M 27/006 604/8 |
| 2008/0200915 | A1 | 8/2008 | Globerman et al. | |
| 2013/0150654 | A1 | 6/2013 | Stanfield | |
| 2013/0331892 | A1 | 12/2013 | Peterson et al. | |
| 2014/0276347 | A1 | 9/2014 | Stone | |
| 2015/0246234 | A1 | 9/2015 | Hazard et al. | |
| 2016/0015893 | A1* | 1/2016 | Hoyt | A61B 17/3472 604/66 |
| 2017/0319831 | A1* | 11/2017 | Gill | A61M 27/006 |
| 2018/0264240 | A1* | 9/2018 | Heilman | A61M 27/006 |
| 2019/0151239 | A1* | 5/2019 | Abrams | A61P 25/08 |
| 2021/0401417 | A1* | 12/2021 | Shipp | A61B 17/0057 |
| 2022/0370240 | A1* | 11/2022 | Wong | A61B 8/0808 |
| 2023/0263515 | A1* | 8/2023 | Fell | A61B 17/0401 |

FOREIGN PATENT DOCUMENTS

| | | | |
|---|---|---|---|
| WO | 2020198289 | A1 | 10/2020 |
| WO | 2021195225 | A1 | 9/2021 |
| WO | 2023/164406 | A2 | 8/2023 |
| WO | 2023/164406 | A3 | 10/2023 |

OTHER PUBLICATIONS

Written Opinion of related PCT/US2023/062813, mailed on Sep. 7, 2023, 4 pages.

Wilson, Mark Howard, “A Technical Drawing of the Clutch Mechanism of a Perforator Drill Bit Courtesy of Fig3” Apr. 2012, Retrieved on Apr. 9, 2025, from https://www.researchgate.net/figure/A-technical-drawing-of-the-clutch-mechanism-of-a-perforator-drill-bit-courtesy-of_fig3_236304981, 10 pages.

Willis-Knighton Cardiology. “Atrial Septal Defect (ASD)” Retrieved on Apr. 9, 2025, from https://www.wkcardiology.com/services/conditions/Atrial-Septal-Defect-ASD, 6 pages.

Integra. “Codman Holter Rickham Reservoir” Retrieved on April 9. 2025, from https://products.integralife.com/codman-holter-rickham-reservoir/product/hydrocephalus-accessories-codman-reservoirs-codman-holter-rickham-reservoir, 1 page.

European Patent Office Partial Search Report dated Jan. 23, 2026 for EP 23760825, 12 pages.

Extended European Search Report, corresponding to EP 23760825.2, dated May 20, 2026.

* cited by examiner

SYSTEMS AND METHODS FOR DRAINING CEREBROSPINAL FLUID

CROSS-REFERENCE TO RELATED APPLICATIONS

The present application is a continuation of U.S. patent application Ser. No. 18/841,260, filed on Aug. 23, 2024, which is a national phase of the pending International Application PCT/US2023/062813 filed on Feb. 17, 2023, which is based on and claims priority from U.S. Patent Application Ser. No. 63/314,232, filed on Feb. 25, 2022, the entire disclosure of each of which is incorporated herein by reference.

STATEMENT REGARDING FEDERALLY SPONSORED RESEARCH

N/A.

BACKGROUND

Hydrocephalus is a common chronic condition in which the normal drainage pathway of cerebrospinal fluid ("CSF") is disrupted. Thus, hydrocephalus can lead to an abnormal accumulation of CSF in the brain, which can increase intracranial pressure ("ICP") to the point of irreversible brain injury, and even death. Typically, hydrocephalus is treated using a nearly 70-year-old technique, which involves placing a shunt to drain the CSF fluid from the brain to the patient's circulatory system (e.g., so the drained CSF can be reabsorbed by the patient's body). However, placing the shunt typically requires inserting tubing through the brain tissue until the tubing enters a ventricle. At this point, the CSF can drain from the ventricle, through the tubing, and into the circulatory system (e.g., via the abdomen).

In some cases, the insertion of the tubing through the brain tissue can cause complications, including brain injury, bleeding, seizures, infections, and intellectual deterioration. In fact, it is not uncommon after placement of a shunt that the tubing of the shunt becomes obstructed by brain tissue debris (e.g., the brain tissue debris blocking the appropriate draining of CSF), which can inevitably lead to the patient undergoing subsequent surgical procedures to fix the blockage. Thus, it would be desirable to have improved systems and methods for draining cerebrospinal fluid.

SUMMARY OF THE DISCLOSURE

Some embodiments of the disclosure provide an implant system. The implant system can include an implant. The implant can include a body defining a first end and a second end opposite the first end. The body can include an exterior surface including threads. The implant system can include a needle removably coupled to the body and extending past the second end of the body. The body can be configured to be driven into an opening in a bone to place the implant into the bone, thereby securing the implant to the bone. The body can be configured to be driven into the opening in the bone such that the needle pierces a tissue adjacent to the bone thereby placing an end of the needle into an anatomical cavity.

Some embodiments of the disclosure provide a drill head. The drill head can include a first drill bit having a first bore, and a second drill bit configured to be received within the first bore of the first drill bit. The second drill bit can be coaxial with the first drill bit. An end of the second drill bit can extend past an end of the first drill bit. The end of the second drill bit can have a protrusion. The first drill bit and the second drill bit can be configured to create a bore in the bone. When the protrusion of the second drill bit creates a hole in the bone that is coaxial to the bone, the second drill bit can translate rearwardly within the bore away from the bone of the patient to prevent the second drill bit from contacting the dura mater. A width of the hole can be smaller than a width of the bore.

Some embodiments of the disclosure provide an implant method. The implant method can include driving a body of an implant into an opening in a bone to place the implant into the bone, thereby securing the implant to the bone. The implant can include a body defining a first end and a second end opposite the first end, the body including an exterior surface including threads and a needle removably coupled to the body and extending past the second end of the body. The implant method can also include piercing, with the needle by driving the body into the opening in the bone, a tissue adjacent to the bone thereby placing an end of the needle into an anatomical cavity.

Some embodiments of the disclosure provide a method of operating a drill head. The method of operating a drill head can include creating a bore in a bone using a first drill bit and a second drill bit. The first drill bit can have a first bore and the second drill bit can be configured to be received within the first bore of the first drill bit, the second drill bit being coaxial with the first drill bit, and an end of the second drill bit extending past an end of the first drill bit, the end of the second drill bit having a protrusion. The method of operating a drill head can also include creating a hole in the bone using the protrusion of the second drill bit which is coaxial to the bone such that the second drill bit translates rearwardly within the bore away from the bone to prevent the second drill bit from contacting the dura mater, a width of the hole being smaller than a width of the bore.

The present disclosure's foregoing and other aspects and advantages will appear from the following description. In the description, reference is made to the accompanying drawings that form a part hereof, and in which there is shown by way of illustration one or more exemplary versions. These versions do not necessarily represent the full scope of the disclosure.

BRIEF DESCRIPTION OF THE DRAWINGS

The following drawings are provided to help illustrate various features of non-limiting examples of the disclosure. They are not intended to limit the scope of the disclosure or exclude alternative implementations.

DETAILED DESCRIPTION OF THE PRESENT DISCLOSURE

As described above, conventional shunts for treating hydrocephalus typically undesirably traverse the brain tissue, leading to brain damage, including brain injury, bleeding, seizures, infections, and intellectual deterioration. Some embodiments of the disclosure provide advantages to these issues (and others) by providing improved systems and methods for draining cerebrospinal fluid. For example, some embodiments of the disclosure provide an implant system that can drain CSF fluid from the cisterna magna of the brain, which can provide an implant location that does not require traversing (and possibly damaging brain tissue), and that is less likely to become clogged with biological debris (e.g., because the CSF in the cisterna magna is less likely to have suspended biological particulates). In particular, the subarachnoid space contains more than two-thirds of the volume of CSF and does not collect debris or cells from the choroid plexus, which is often the source of debris that blocks conventional shunt systems. Thus, this implant system is a safe and effective way of accessing CSF from the cisterna magna for the purposes of long-term CSF diversion to treat the condition of hydrocephalus.

This implant system can also serve the purpose of a reservoir and access point for providing treatments (e.g., repeat or ongoing treatments), including chemotherapeutic or biological therapies that may be required to be administered into the intrathecal space. In addition, the implant system also has several other advantages, including: (1) not traversing brain tissue (e.g., because it does not enter the brain, which is advantageous but it also eliminates the inflammation and potential clogging of the catheter with brain matter), (2) the implant location described herein to access CSF from the cisterna magna is advantageous because CSF can flow from the natural brain pulsations and pressure differentials of the CSF (e.g., rather than relying on gravity and siphoning of fluids in the conventional systems and thus eliminating the need for complex valve and anti-siphoning systems thereby decreasing the implant system total footprint), and (3) CSF can be shunted directly into the venous system for drainage, which is what typically happens in healthy brains. Thus, regarding point (3), given the collinear relationship between the inflow and outflow systems of this implant system, the only valve that may be needed will be on the distal portion (venous) of the catheter, which can prevent the backflow of blood into the CSF in the unlikely event that venous pressure exceeds the pressure in the subarachnoid space.

Figures 1A, 1B:
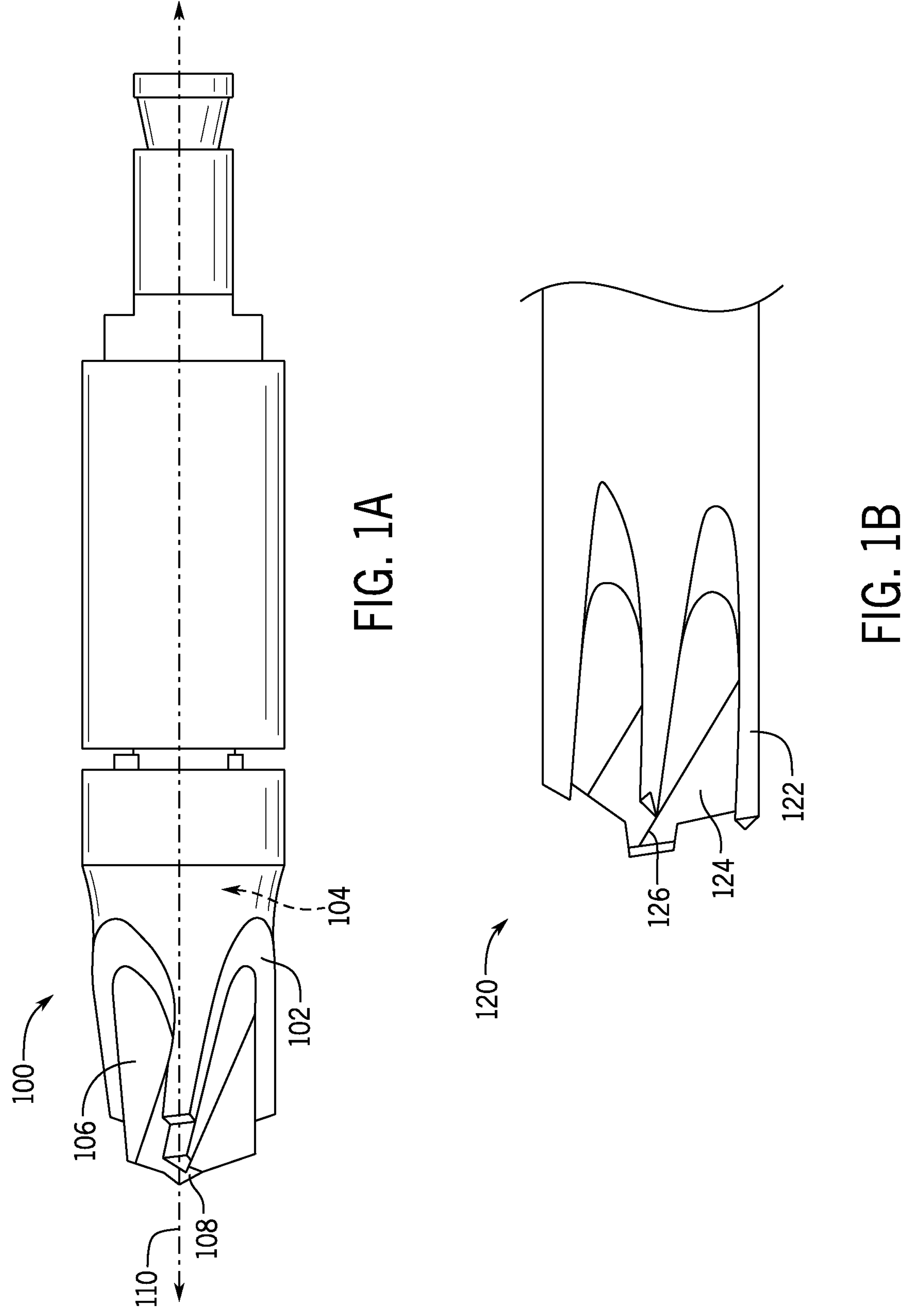
FIG. 1A shows an illustration of a drill head.
FIG. 1B shows an illustration of another drill head.

FIG. 1A shows an illustration of a drill head 100. The drill head 100 can include a drill bit 102 having a bore 104, and a drill bit 106 configured to be received within the bore 104 of the drill bit 102. As shown in FIG. 1, the drill bit 106 can be coaxial with the drill bit 102, with the drill bit 106 having a smaller width than the drill bit 102. In some cases, the drill bit 106 can extend past an end of the drill bit 102 (e.g., configured to contact a patient's bone). In some embodiments, the drill bit 106 can be biased to a position in which the drill bit 106 is forced further out of the bore 104 (e.g., as compared to a position without biasing). For example, when the drill head 100 is pressed against a bone of a patient during drilling of the bone, the drill bit 106 translates further out of the bore 104 (e.g., due to a spring that forces the drill bit 106 further out of the bore 104 when a force presses on the drill bit 106). In this way, as the drill bit 106 rotates to create a hole (or opening) in the bone, the resistive force that forced the drill bit 106 further out of the bore 104 is removed so that the drill bit 106 retracts away from the bone into the bore 104. This can ensure that the drill bit 106 does not undesirably perforate the dura mater when a hole is created in the bone. In some configurations, the drill bits 102, 106 can function in a similar manner and can include similar components to the cranial perforator described in U.S. Pat. No. 4,600,006, which is incorporated herein by reference.

As shown in FIG. 1A, the drill bit 106 can have a protrusion 108 that is positioned at a distal end of the drill bit 106. For example, the protrusion 108 can intersect a long axis 110 of the drill bit 106, in which the drill bit 106 rotates around the long axis 110. While the protrusion 108 is illustrated in FIG. 1A as being pyramidal, in other cases, the protrusion 108 can be implemented in different ways. For example, FIG. 1B shows a schematic illustration of a drill head 120, which can be similar the drill head 100. The drill head 120 can include drill bits 122, 124, with the drill bit 122 being coaxial to the drill bit 124 and surrounding the drill bit 124. The drill bit 124 can include a protrusion 126 that can be positioned at a distal end of the drill bit 124 and can have a flat or an angled surface. Regardless of the configuration, the protrusions 108, 126 can be advantageous in that, compared to other cranial perforators that create a bone plate with a concave central portion, the protrusions 108, 126 advantageously create a central hole (e.g., in place of the concave central region), which can be used for accessing and piercing the dura mater so that an implant (described below) can be inserted for removing CSF.

Figures 1C, 1D:
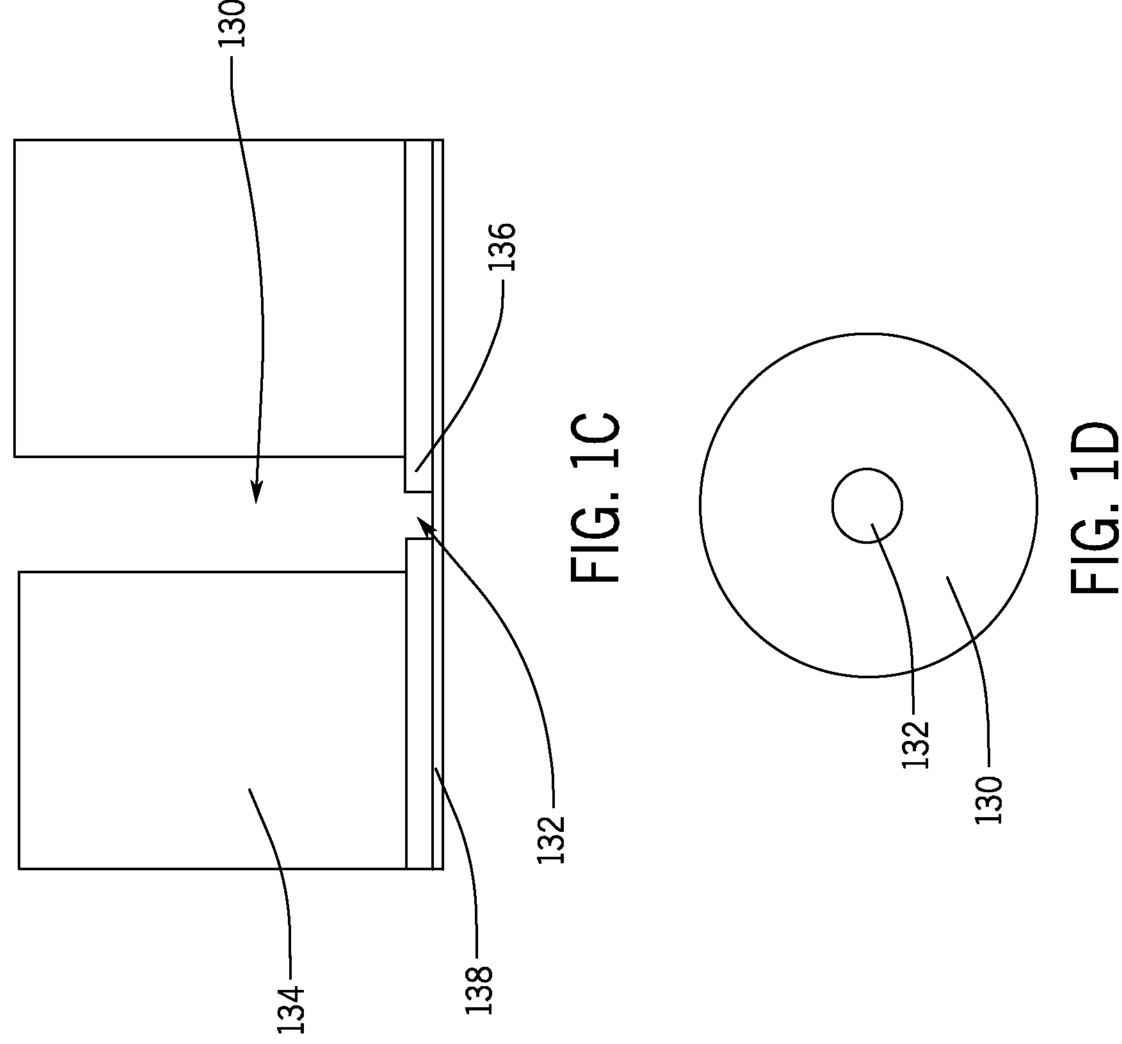
FIG. 1C shows a schematic illustration of a side view of a bore and a hole created by a drill head.
FIG. 1D shows an illustration of a top view of the bore and the hole of FIG. 1C.
Figure 2:
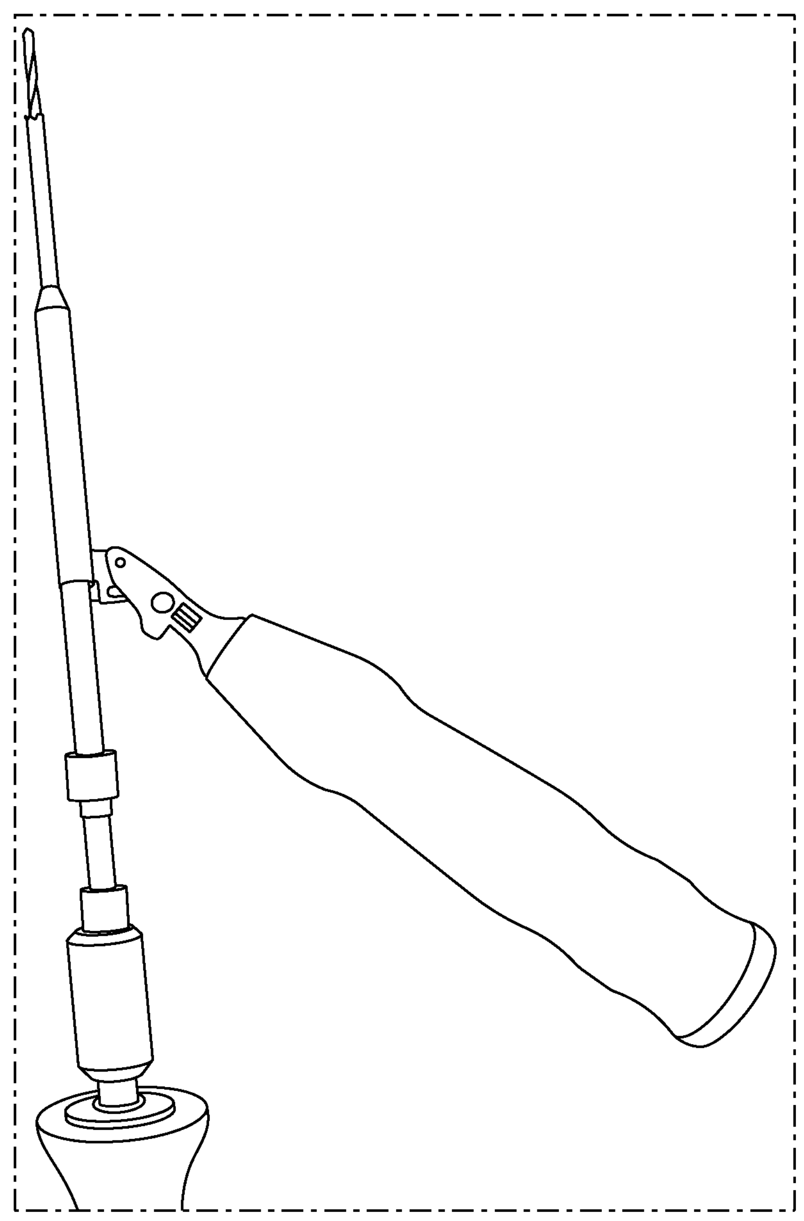
FIG. 2 shows a photograph of a navigation device to drill a hole in bone, and to deploy an implant.
Figure 3:
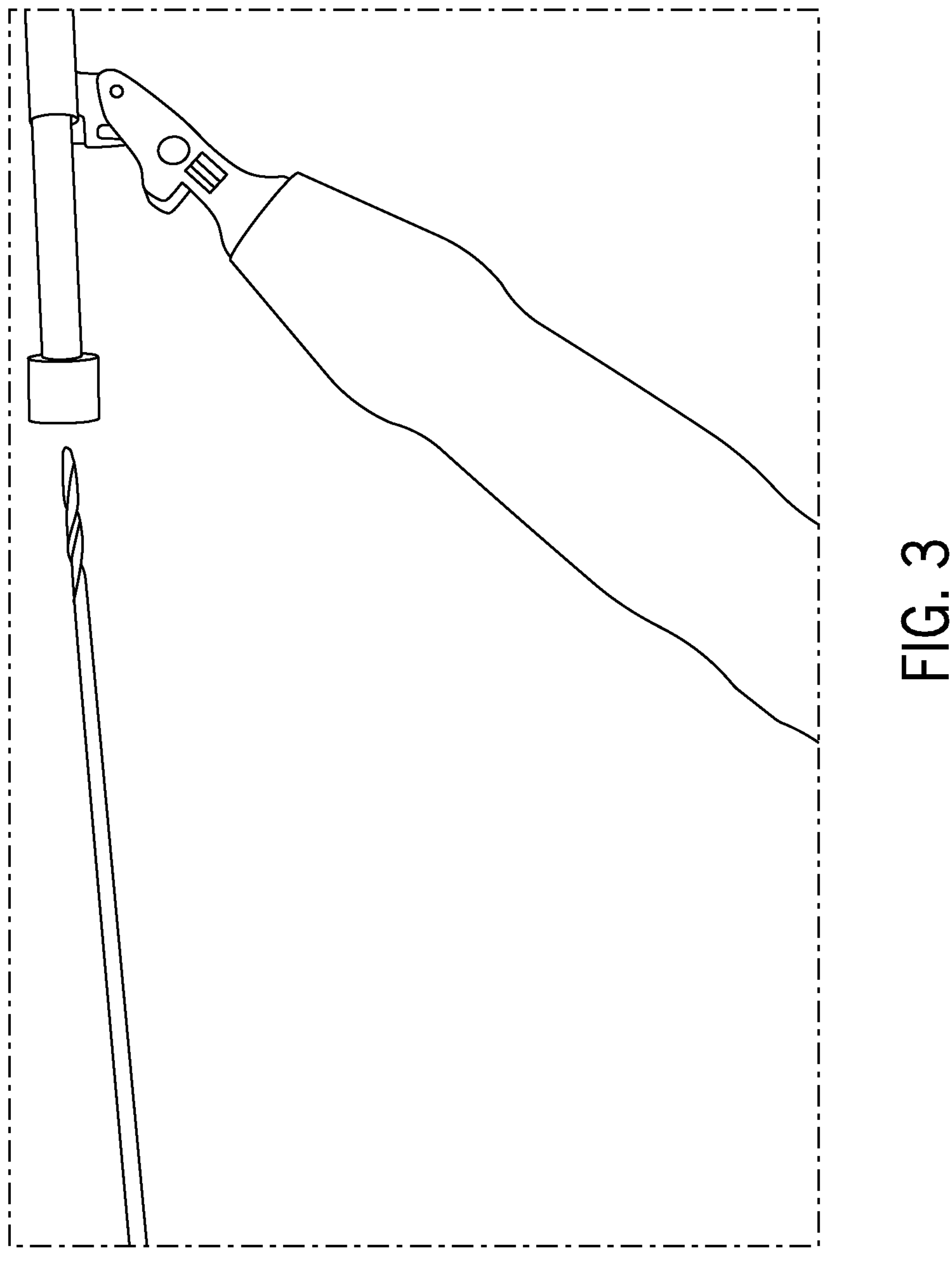
FIG. 3 shows a photograph of an enlarged view of the navigation device of FIG. 2 with the drill bit being inserted.
Figure 4:
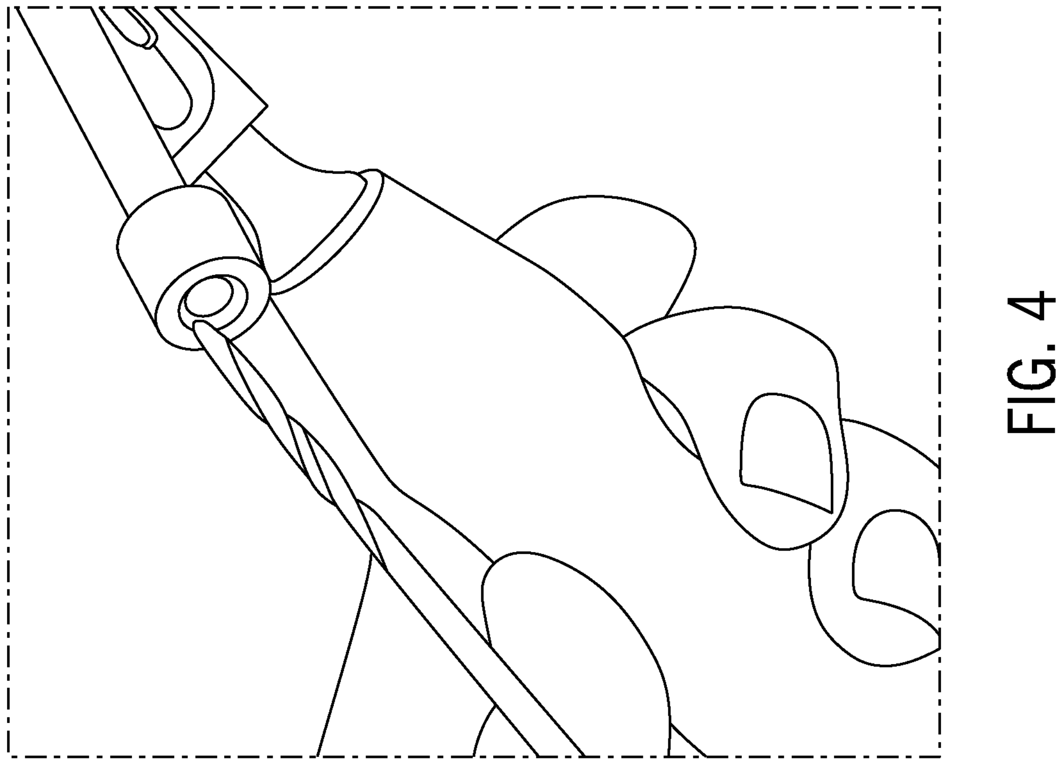
FIG. 4 shows a photograph of a rear isometric view of the navigation device of FIG. 2 with drill bit being inserted.
Figures 5, 6, 7:
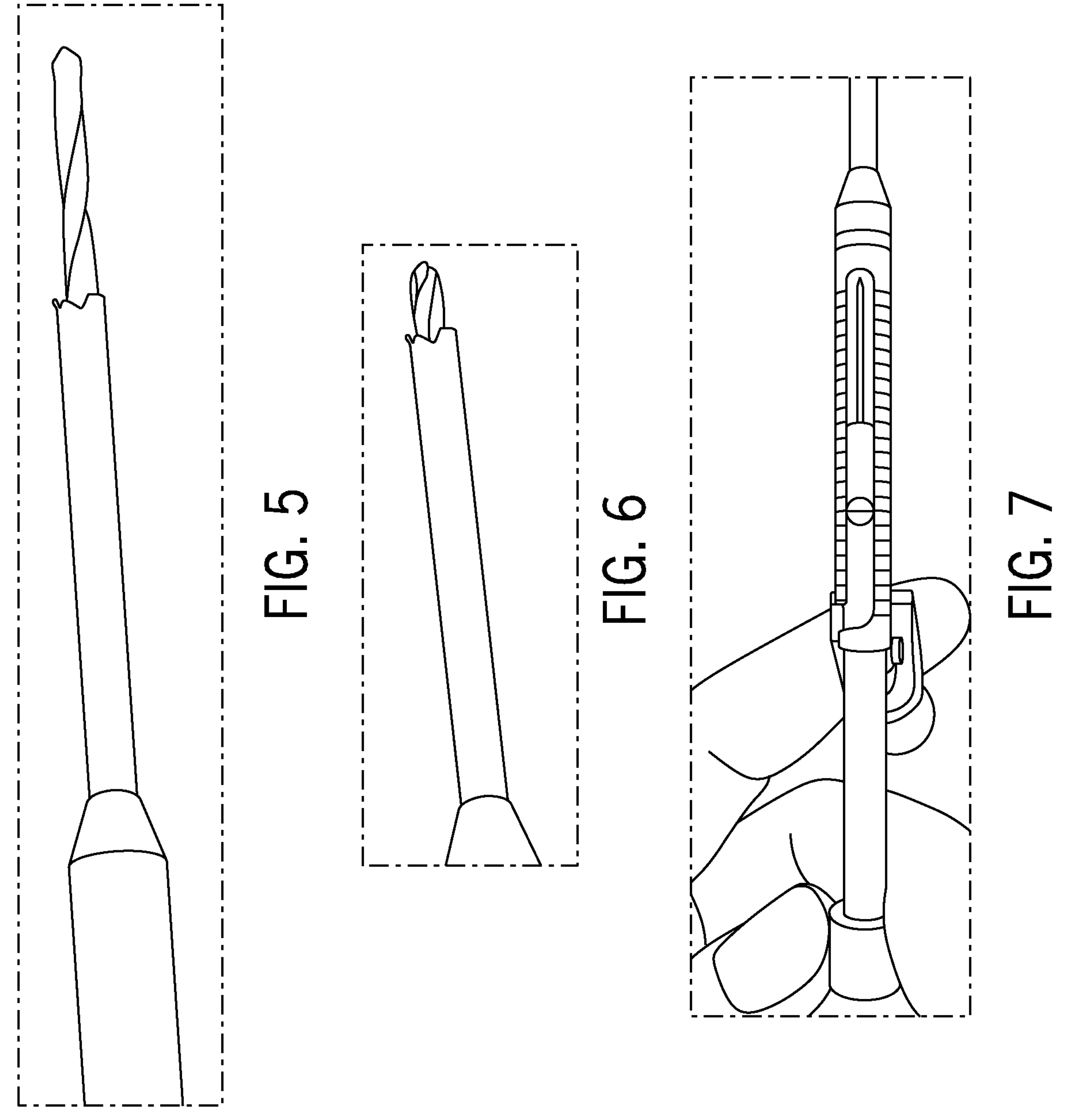
FIG. 5 shows a photograph of an enlarged side view of the drill head of the navigation device of FIG. 2, with the drill bit in an extended position.
FIG. 6 shows a photograph of an enlarged side view of the drill head of the navigation device of FIG. 2, with the drill bit in a retracted position.
FIG. 7 shows a photograph of a side view of the navigation device of FIG. 2.

FIGS. 1C and 1D schematically depict a bore of the type that can be created by either of the drill heads 100, 120. As shown in FIG. 1C, a bore 130 and a hole 132 have been created in a bone 134 (e.g. the posterior arch), with the bore 130 and the hole 132 collectively forming a shelf 136; while the shelf 136 is depicted in FIG. 1C as having an approximately square profile, the final profile will be determined by the shape of the drill bit 106, 124 including the protrusions 108, 126. To create the bore 130 and the hole 132 using the drill head 120 of FIG. 1B, the drill head 120 is advanced into the bone 134 to begin to form the bore 130. Then, as the drill bits 122, 124 continue to remove bone material, the protrusion 126 begins to start forming the hole 132 at the edge of the bone 134. Once the protrusion 126 exits the bone 134 and forms the hole 132, the resistive force provided by the bone 134 is removed, which retracts the drill bit 124 thereby preventing the drill bit 124 from piercing the dura mater 138 or other tissue that is positioned adjacent to the bone 134. Thus, the protrusion 126 forms the hole 132 in the bone, while the drill bits 122, 124 form the bore 130 while leaving the shelf 136 adjacent the hole 132. In some configurations, the shelf 136 can provide additional support for an implant (described in more detail below), and can provide a stop to block further advancement of the implant towards the dura mater 138. As shown in FIG. 1C, the hole 132 is coaxial to the bore 130, and the hole 132 has a smaller diameter than the bore 130.

In some embodiments, the distance between a distal end of the drill bit 106 and a distal end of the drill bit 102 can define a thickness of the shelf 136. In this way, the thickness of the shelf 136 can be predetermined, regardless of the specific patient, thereby creating uniform thicknesses of the shelf 136 regardless of variations in anatomical structures between different patients. In some cases, the thickness of the shelf 136 can be less than 1 mm, less than 2 mm, or any other thickness determined based on the type of bone, the size of the patient, and other considerations.

FIGS. 2-7 show various views of a navigation device to drill out a hole in a bone of the patient and to deploy an implant described herein. For example, as shown in these figures, a bore of the navigation device can receive a drill bit (e.g., a drill bit of the drill head 100, or the drill head 120) until the drill bit protrudes through the bore, and a grading system of the navigation device can limit the amount the drill pit extends out of the bore. In some cases, the implants described herein can be advanced through the bore, and the other systems described herein (e.g., the plugs) can be advanced through the bore.

Figure 8:
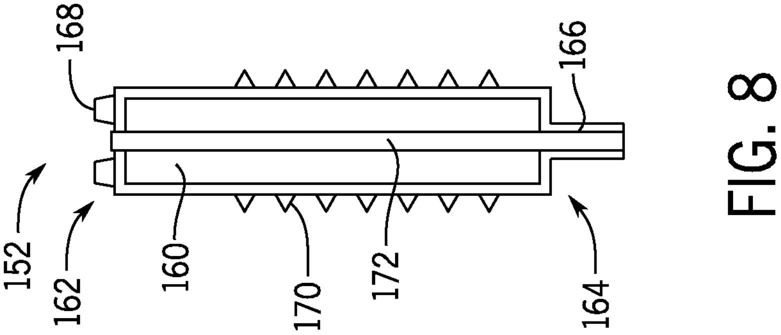
FIG. 8 shows a schematic illustration of an implant.

FIG. 8 shows a schematic illustration of an implant 152. As shown in FIG. 8, the implant 152 can include a body 160 having an end 162 and an opposite end 164, an extension 166, and a tool interface 168. In some cases, an external surface of the body 160 can include threads 170 (e.g., male threads) to threadingly engage a bone of a patient. For example, as the body 160 is rotated and advanced into a hole of the bone (e.g., a hole created by the drill head 100 described above), the threads 170 of the body 160 cut the bone at the hole (e.g., a surface of the bone that defines the hole) thereby creating corresponding threads in the bone. In this way, the implant 152 and, in particular the body 160 of the implant 152 can be better secured to the bone at the hole of the bone. In some embodiments, the body 160 of the implant 152 can be cylindrical. However, in other configurations, the body 160 can have different shapes (e.g., a prism, such as an octagonal prism). In some cases, when the body 160 has a cylindrical shape, the threads 170 can better engage the bone at the hole to create the corresponding threads in the bone.

In some embodiments, the extension 166 can be coupled to the body 160 (or can be integrally formed with the body 160, so that the body 160 and the extension 166 are a single monolithic component). The extension 166 can be coupled to the body 160 at the end 164 of the body 160 (e.g., a distal end of the body 160). Thus, the extension 166 can extend past a surface of the end 164 of the body 160. As shown in FIG. 8, the extension 166 has a smaller width than the body 160 (e.g., with the body 160 having a substantially (i.e., deviating by less than 10 percent from) uniform width along the length of the body 160). In this way, the extension 166 can extend through the hole 132 of the bone 134, but the body 160 is blocked from extending through the hole 132 (e.g., because the body 160 can have a larger width than the hole 132).

In some embodiments, the implant 152 can include a bore 172 that can extend entirely through the body 160 of the implant 152, and can extend entirely through the extension 166 of the implant 152. In this way, and as described in more detail below, the bore 172 can receive a needle for perforating the dura mater during, for example, placing of the implant 152, and can receive, in place of the needle, an insert that can drain CSF from the subarachnoid space.

In some embodiments, the tool interface 168 can be coupled to the body 160. For example, the tool interface 168 can be positioned at the end 162 of the body 160 and coupled to a surface (e.g., a horizontal surface) of the body 160. The tool interface 168 can be implemented in different ways but can be generally configured to engage a tool adapter, such as, for example, a socket, an impact driver, etc., to more easily transmit torque from a tool (e.g., a ratchet) to the body 160 of the implant 152. For example, the tool interface 168 can be a protrusion (e.g., a hexagonal protrusion) that engages with a ratchet socket so that the torque from the ratchet is more easily transmitted to the body 160 (e.g., via the tool interface 168). In this way, with the tool interface 168 engaged with a ratchet socket, as the ratchet is rotated in a first direction, the socket drives rotation of the body 160 of the implant 152.

Figure 9:
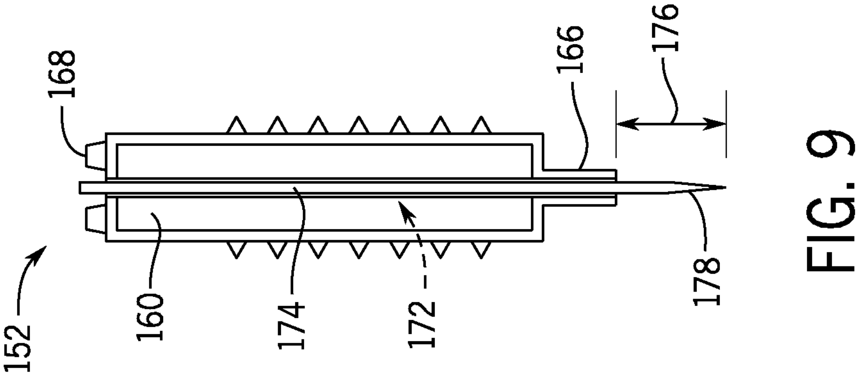
FIG. 9 shows a schematic illustration of an implant with a needle deployed therein.

FIG. 9 shows the implant 152 and a needle 174 (ratchet not shown in this view) placed in the implant 152 as would be done when the implant 152 is initially inserted into the bore 130 in the bone 134. For example, the needle 174, which can be coupled to a ratchet, can be inserted into the bore 172 of the implant 152, and can extend past the end 164 of the body 160, and a free end of the extension 166 (e.g., by a particular amount 176). Note that the dimensions depicted in FIG. 9 are exaggerated in the vertical direction for illustrative purposes to better present the individual components. However, in the actual implant the extension 166 is slightly longer than the thickness of the bone shelf 136 (see FIG. 1C) so that the extension 166 extends only a short distance (e.g. 1-2 mm) past the bone when the implant 152 is in its final position (see FIG. 14). Similarly, the needle 174 only extends a short distance beyond the end of the extension 166 (e.g. about 1 mm or less) so that the needle 174 is just long enough to puncture the tissue adjacent to the bone. For example, the length of the needle 174 can be greater than the length of the body 160, and greater than the length of the body 160 and the extension 166. In this way, the needle 174 can pierce the dura mater to bring the cisterna magna into fluid communication with a reservoir. In some configurations, the needle 174 can have a lumen that provides fluid communication between an end of the needle 174 and the end of the body 160 of the implant 152. In this way, as the implant 152 is placed and a sharp tip 178 of the needle 174 pierces the dura mater, CSF from the cisterna magna flows through the lumen of the needle 174 and exits the body 160 of the implant 152 (e.g., via a port) to provide an indication to the surgeon that the implant has advanced far enough (and should not be advanced further). In other configurations, the needle 174 does not have a lumen. For example, in this case, the needle 174 can have a cross-section that is solid along a portion or the entire length of the needle 174.

Figure 10:
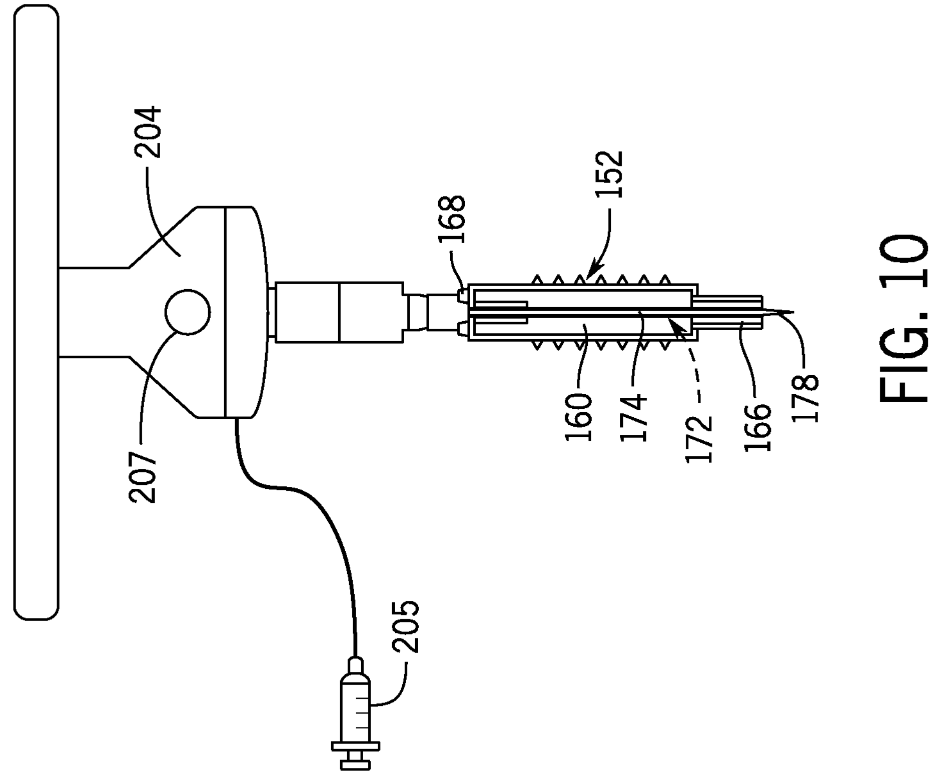
FIG. 10 shows a front view of a ratchet engaged with a body of the implant of FIG. 8.

FIG. 10 shows a front view of a ratchet 204 engaged with the body 160 of the implant 152. In particular, the needle 174 is coupled to the ratchet 204 (e.g., at an end of the needle 174), and a socket of the ratchet 204 is engaged with the tool interface 168 of the body 160. Once a bore and a hole is formed in the bone (e.g., the bore 130 and the hole 132, see FIG. 1C), the needle 174 can be inserted into the bore 172 of the body 160 (e.g., such that the needle 174 extend past a free end of the extension 166) and the implant 152 with the needle 174 disposed therein can be attached to the ratchet 204. To deliver the implant 152, the ratchet 204 can be twisted to rotate the implant 152 with the needle 174 positioned therein, until the sharp end 178 of the needle 174 pierces the dura mater. When the sharp end 178 of the needle 174 pierces the dura mater, the extension 166 passes through the newly formed hole in the dura mater, thereby bringing the needle 174 and the extension 166 into fluid communication with the CSF of the patient. In some cases, a channel (not shown) that is in fluid communication with an opening in the needle 174 can be directed through the ratchet 204 (e.g., at the socket of the ratchet) so that the channel can be in fluid communication with a syringe 205 (or other fluid receiving device such as, for example, a reservoir, a tube, etc.). In this way, when the dura mater is punctured by the needle 174, fluid flows through the lumen of the needle 174, through the channel in the ratchet 204, and into the syringe 205. At this point, the surgeon knows that the implant 152 should not be advanced any further due to the appearance of fluid in the syringe 205. In other words, the presence of the fluid out of the implant 152 and out of the channel indicates to the surgeon that the advancement of the implant 152 should be halted.

In some embodiments, the ratchet 204 can include a channel 207 that can extend through the ratchet 204 towards an end of the ratchet 204 that engages the tool interface 168 of the implant 152. In this way, an imaging device (e.g., a camera or a fiber optic device coupled to a camera) can be directed through the channel 207, and can view the implant 152, to, for example, verify the placement of the implant 152.

In some configurations, after the implant 152 has been verified to be placed properly (e.g., after CSF is detected), the needle 174 can be removed from the bore 172 of the body 160 of the implant 152. For example, the ratchet 204 can be disengaged from the tool interface 168 (e.g., rotated), and the ratchet 204 can be lifted to remove the ratchet 204 and the needle 174 together. At this point, an open end of the extension 166 is positioned within the subarachnoid space.

Figure 11:
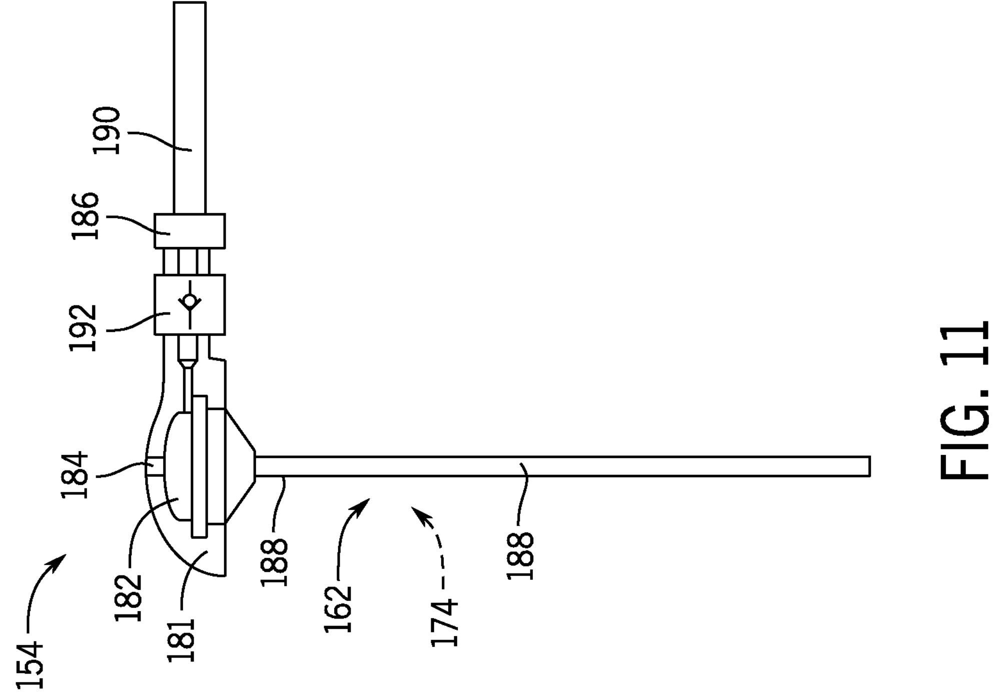
FIG. 11 shows a schematic illustration of a reservoir system.

FIG. 11 shows a schematic illustration of a reservoir system 154. The reservoir system 154 can include a reservoir 181 having an interior volume 182, and ports 184, 186, each of which can be in fluid communication with the interior volume 182. The ports 184, 186 can generally provide different flow paths for fluid (e.g., CSF) within the reservoir system 154, and each of the ports 184, 186 can be oriented in different ways. For example, the port 184 can be substantially perpendicular to the port 186. In some cases, the reservoir system 154 can include hollow tubes 188, 190, each of which can be connected to a port in fluid communication with the interior volume 182 of the reservoir system 154. In this way, each hollow tube 188, 190 can provide a flow path for CSF through the reservoir system 154. As shown in FIG. 11, the hollow tube 188 can be coupled to an end of the reservoir 181 opposite the port 184. In other words, an axis of the reservoir system 154 can extend through the port 184 and the lumen of the hollow tube 188. In some cases, the hollow tube 190 can be coupled to the port 186, for example, to more easily secure the hollow tube 190 after placement of other components of the reservoir system 154 (e.g., the hollow tube 188). In some cases, the hollow tube 190 can be oriented in different ways (e.g., the hollow tube 190 can be flexible), while in other cases, the tube 190 can be resisted from being oriented in different ways (e.g., the hollow tube 190 can be rigid).

As shown in FIG. 11, the reservoir system 154 can optionally include a one-way valve 192 (e.g., a check valve) that is positioned between the ports 184, 186 that can allow flow of fluid in a first direction (e.g., from the port 184 to the port 186) and can block flow of fluid in a second direction (e.g., from the port 186 to the port 184) opposite the first direction. While the one-way valve 192 is illustrated as being part of the reservoir system 154, in other configurations, the one-way valve 192 (or another one-way valve) may be located in another part of the implant system 150.

In some embodiments, the port 184 can be advantageous. For example, a bioactive agent (e.g., a biological therapeutic, a chemotherapy agent, etc.) can be introduced through the port 184 into the interior volume 182 and through the tube hollow 188 (and thus through the implant 152, and through the bone 134) to the target site (e.g., the cisterna magna). Thus, the reservoir system 154 can provide a reliable and reusable port for introducing a pharmacological or other therapeutic treatment to the patient via the implant 152. In addition, in some embodiments, the one-way valve 192 can be selectable between a first position and a second position. In this way, with the reversible one-way valve in the first position (e.g., during treatment with the bioactive agent), the bioactive agent is blocked from flowing through the reversible one-way valve 192. Thus, the bioactive agent is ensured to be directed into the target site (e.g., the cisterna magna) rather than being directed to be absorbed by the body along with the CSF. Then, with the reversible one-way valve in the second position (e.g., after treatment with the bioactive agent), the reversible one-way valve 192 can allow fluid flow in the first direction while blocking fluid flow in the second direction.

Figure 14:
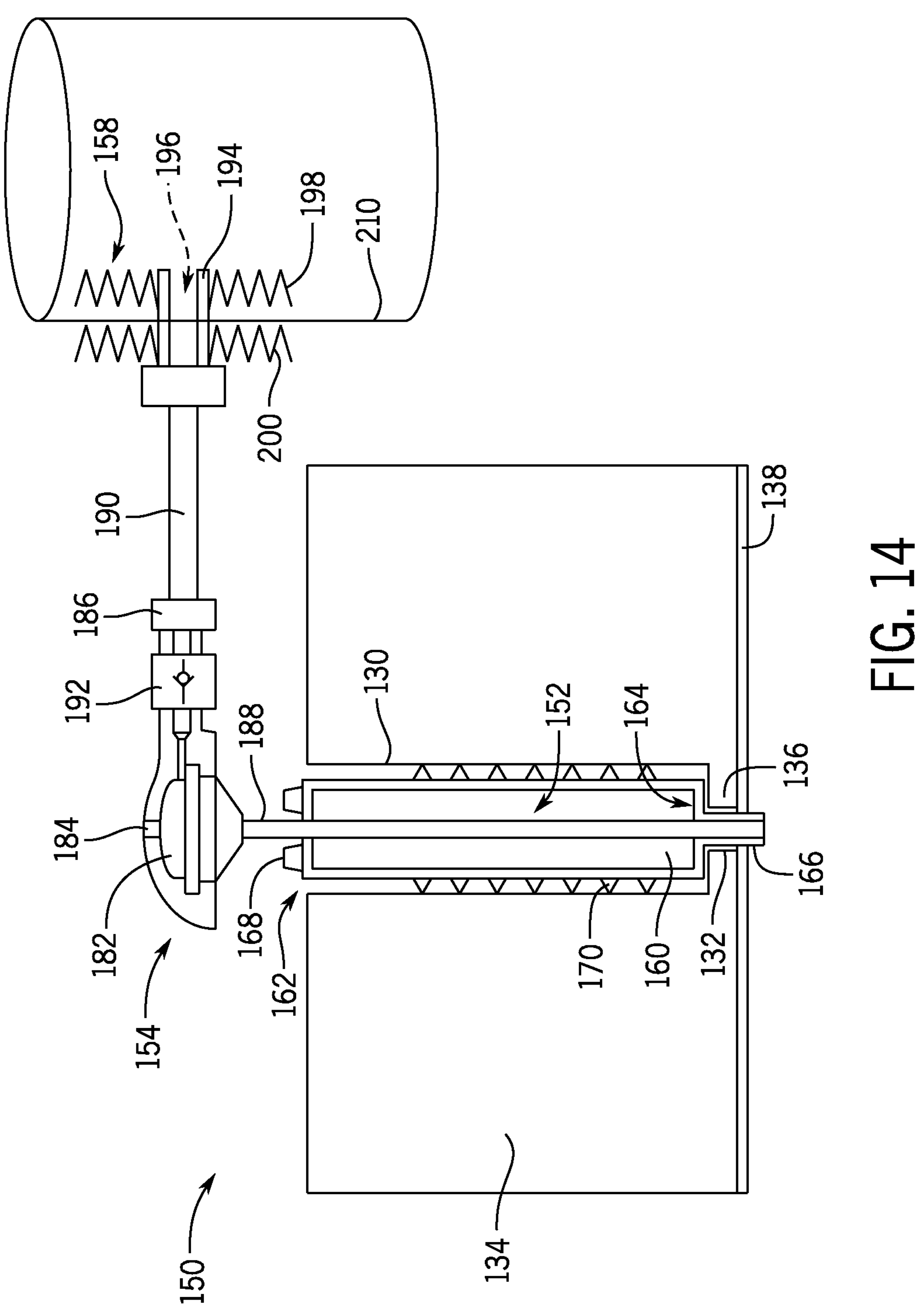
FIG. 14 shows a schematic illustration of an implant system.

In some embodiments, the hollow tube 188 can be inserted through the bore 172 of the body 160 of the implant 152 (see FIG. 14). For example, once the implant 152 has been placed and the needle 174 has been removed, the hollow tube 188 can be advanced into the bore 172 of the body 160 of the implant 152, until, for example, the end of the hollow tube 188 is flush with an end of the extension 166, the end of the hollow tube 188 extends just beyond a free end of the extension 166, or the end of the hollow tube 188 is positioned just behind the extension 166. Regardless of the configuration, the hollow tube 188 can provide a flow path for CSF. For example, CSF can flow through the hollow tube 188, into the interior volume 182, out the port 186, and through the hollow tube 190. In some cases, the hollow tube 188 can be fixedly coupled to the reservoir 181, or in other cases can be removably coupled to the reservoir 181. Regardless of the configuration, the hollow tube 188 can be advantageous in that, if the hollow tube 188 becomes clogged (e.g., from particulates in the CSF), the implant 152 does not need to be removed from the patient. Rather, the hollow tube 188 can be removed from the bore 172, and a replacement hollow tube 188 (e.g., with another reservoir system 154) can be advanced through the bore 172 in a relatively minor procedure.

Figure 12:
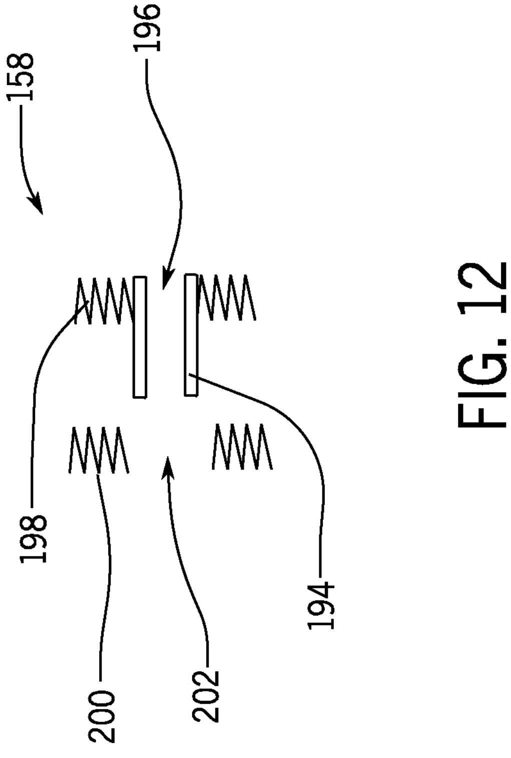
FIG. 12 shows a schematic illustration of a plug before engagement with a wall of a blood vessel and with the mechanical stop in the compressed state.

As described in more detail below, the hollow tube 190 is fluidly coupled to a vessel such as the jugular vein to allow drainage of CSF. The tubing (e.g., an extension of the hollow tube 190 or another tube that is coupled to the hollow tube 190) is coupled to the vessel wall by a plug which can be delivered to the site of attachment using a catheter and guidewire arrangement and attached on the inside and the outside of the vessel by anchoring mechanisms. FIGS. 12 and 13 show a schematic illustration of a plug 158. The plug 158 can include a body 194, a bore 196 directed entirely through the body 194, a mechanical stop 198, and a retainer 200. The mechanical stop 198 can be coupled to the body 194 so that the mechanical stop 198 extends radially away from the bore 196 of the body 194. For example, the mechanical stop 198 can include a hole. The body 194 can be inserted into the hole of the mechanical stop 198 with the mechanical stop 198 coupled to the body 194 at the hole of the mechanical stop 198. In some cases, the mechanical stop 198 can be made of a self-expanding material (e.g. a mesh made of a resilient wire such as nitinol) that is delivered in a compressed state and deployed into an expanded state after being placed adjacent to the vessel wall. For example, the mechanical stop 198 in the compressed state can have a width that is smaller than a hole in a blood vessel wall 210 (e.g., a vein such as the external jugular vein), whereas the mechanical stop 198 in the expanded state can have a width that is larger than the hole in the blood vessel. In this way, in the compressed state, the mechanical stop 198 can be inserted through the hole in the blood vessel so that the mechanical stop 198 is positioned within the blood vessel. Correspondingly, after the mechanical stop 198 self-expands into the expanded state, the mechanical stop 198 can extend beyond the hole in the blood vessel and can contact a wall of the blood vessel. In this way, the mechanical stop 198 can block retracting of the plug 158 out of the hole of the blood vessel.

Figure 13:
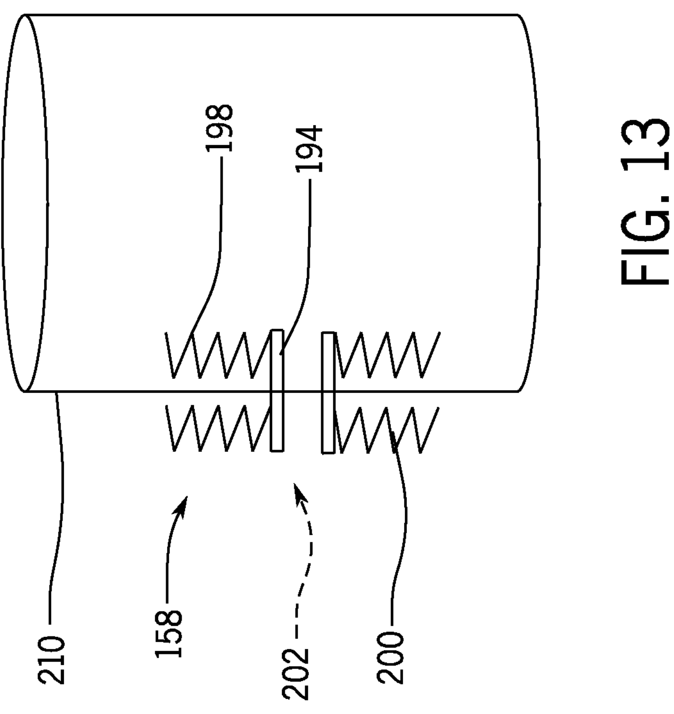
FIG. 13 shows the plug of FIG. 12 engaged with a blood vessel wall.

In some embodiments, the retainer 200 can be coupled to the body 194. For example, the retainer 200 can be removably coupled to the body 194. In some cases, the retainer 200 can include a hole 202, and the body 194 can be inserted into the hole 202 to couple the retainer 200 to the body 194. For example, the hole 202 can have an inner diameter that is smaller (when the retainer 200 is in the expanded state) than an outer diameter of the body 194 so that when the body 194 is inserted into the hole 202 of the retainer 200, the hole 202 contracts such that the retainer 200 constricts around the body 194 to couple the retainer 200 to the body 194. As shown in FIG. 13, after the mechanical stop 198 expands into the expanded state while inside the blood vessel wall 210, the retainer 200 can be advanced along the body 194 until the retainer 200 contacts the wall of the blood vessel. In this way, when the plug 158 is secured to the blood vessel, the mechanical stop 198 is positioned on one side of the blood vessel wall, and the retainer 200 is positioned on an opposite side of the wall of the blood vessel. In other words, the blood vessel wall 210 is positioned between the mechanical stop 198 and the retainer 200 such that the plug is held firmly in place within the vessel wall.

In some cases, the mechanical stop 198 can extend partially (or entirely) around the bore 196 of the body 194. In some embodiments, the mechanical stop 198 can be maintained in the compressed state with a sheath that coaxially surrounds the compressed mechanical stop 198. In this way, the mechanical stop 198 can be selectively expanded to the expanded state (e.g., by removal of the sheath). FIG. 13 shows the plug 158 engaged with a blood vessel wall after delivery. In particular, FIG. 13 shows the mechanical stop 198 in an expanded state and the retainer 200 coupled to the body 194 so that the wall of the blood vessel is positioned between the mechanical stop 198 and the retainer 200.

In some cases, the plug 158 can be implanted by creating a hole in a blood vessel (e.g., by puncturing the blood vessel) and advancing a guidewire through the hole in the blood vessel. Then, the guidewire can be inserted through the bore 196 of the body 194 with the mechanical stop 198 in the compressed state (e.g., by using a sheath), and the body 194 can be advanced until the mechanical stop 198 passes through the hole and into the blood vessel. At this point, the mechanical stop 198 can be expanded (e.g., by removing the sheath), and the mechanical stop 198 in the expanded state can be pulled until the mechanical stop 198 contacts the wall of the blood vessel. Then, the retainer 200 can be engaged with the body 194 and can be advanced until the retainer 200 contacts the wall of the blood vessel. After the plug 158 has been secured to the vessel wall, tubing that is coupled to the hollow tubing 190 can be coupled to the body 194 to complete the fluid coupling between the cisterna magna and the vessel.

In some configurations, similarly to the mechanical stop 198, the retainer 200 (which can be a self-expanding mesh that is made of a resilient wire such as nitinol) can also move from a compressed state to an expanded state. For example, the retainer 200 in the expanded state can have a larger width than the retainer 200 when it is in the compressed state. In some cases, the plug 158 can be deployed using a guidewire. For example, the guidewire with a puncturing device can create a hole in the blood vessel wall 210. Then, the guidewire can pass through the body 194, and the body 194 can be advanced along the guidewire until the mechanical stop 198 in the compressed state, passes through the hole in the blood vessel wall 210. Subsequently, the mechanical stop 198 can be expanded (e.g., by removing a sheath which is around and which had compressed the mechanical stop 198) and can be pulled tensilely. Then, the guidewire can pass through the retainer 200 in the compressed state, and the retainer 200 can be advanced along the guidewire until the retainer 200 contacts (or is positioned proximal to) the blood vessel wall 210 (e.g., with the retainer 200 being positioned on an opposing side of the blood vessel wall 210 as the mechanical stop 198). Subsequently, the retainer 200 can be expanded (e.g., by removing a sheath which surrounds and compresses the retainer 200).

FIG. 14 shows an implant system 150 that can include the implant 152, the reservoir system 154, and the plug 158 deployed within the patient. In some embodiments, after a drill head (e.g., the drill head 100) or other perforator creates the bore 130 and the hole 132 in the bone 134 (e.g., a tubercle such as at the posterior arch), the body 160 of the implant 152 can be driven into the bore 130 of the bone 134 to place the implant 152 into the bone 134, thereby securing the implant 152 to the bone 134. For example, as described above, a tool (e.g., such as a ratchet) can engage the tool interface 168 to rotate the body 160 of the implant 152 with a needle deployed therein, thereby advancing the body 160 through the bore 130 until the needle 174 and the extension 166 extend through the hole 132 and the dura mater 138. In some cases, the extension 166 (and the needle 174) can extend past the distal end of the body 160 a particular amount (e.g., substantially 3 mm, substantially 4 mm, less than 3 mm, less than 4 mm, etc.). In some cases, the extension 166 (and the needle 174) can extend past the dura mater 138 (or other membrane), or the distal surface of the bone 134, a particular amount (e.g., substantially 1 mm, substantially 2 mm, less than 1 mm, less than 2 mm, etc.). In some configurations, the end 164 of the body 160 of the implant 152 can contact the shelf 136 of the bone 134 (e.g., which can block further advancement of the implant 152 further through the bore 130).

In some embodiments, once the needle 174 has been removed from the implant 152, the reservoir system 154 can be coupled to the implant 152, and the hollow tube 190 can be coupled the plug 158 (e.g., after the plug 158 has been placed). For example, the hollow tube 188 of the reservoir system 154 can be inserted into the bore 172 of the body 160 of the implant 152, and subsequently, the plug 158 can be deployed, and the hollow tube 190 can be coupled to the reservoir system 154 (e.g., at the port 186) and the body 194 of the plug 158. In this way, fluid can flow from the anatomical cavity, through the implant 152, through the reservoir system 154, through the hollow tube 190, through the plug 158 and into the blood vessel where the patient's body recycles the fluid. In some embodiments, the implant 152 may be driven into the bone first and the needle 174 may then be inserted into the implant 152 after the implant 152 has been deployed within the bone.

Figure 15:
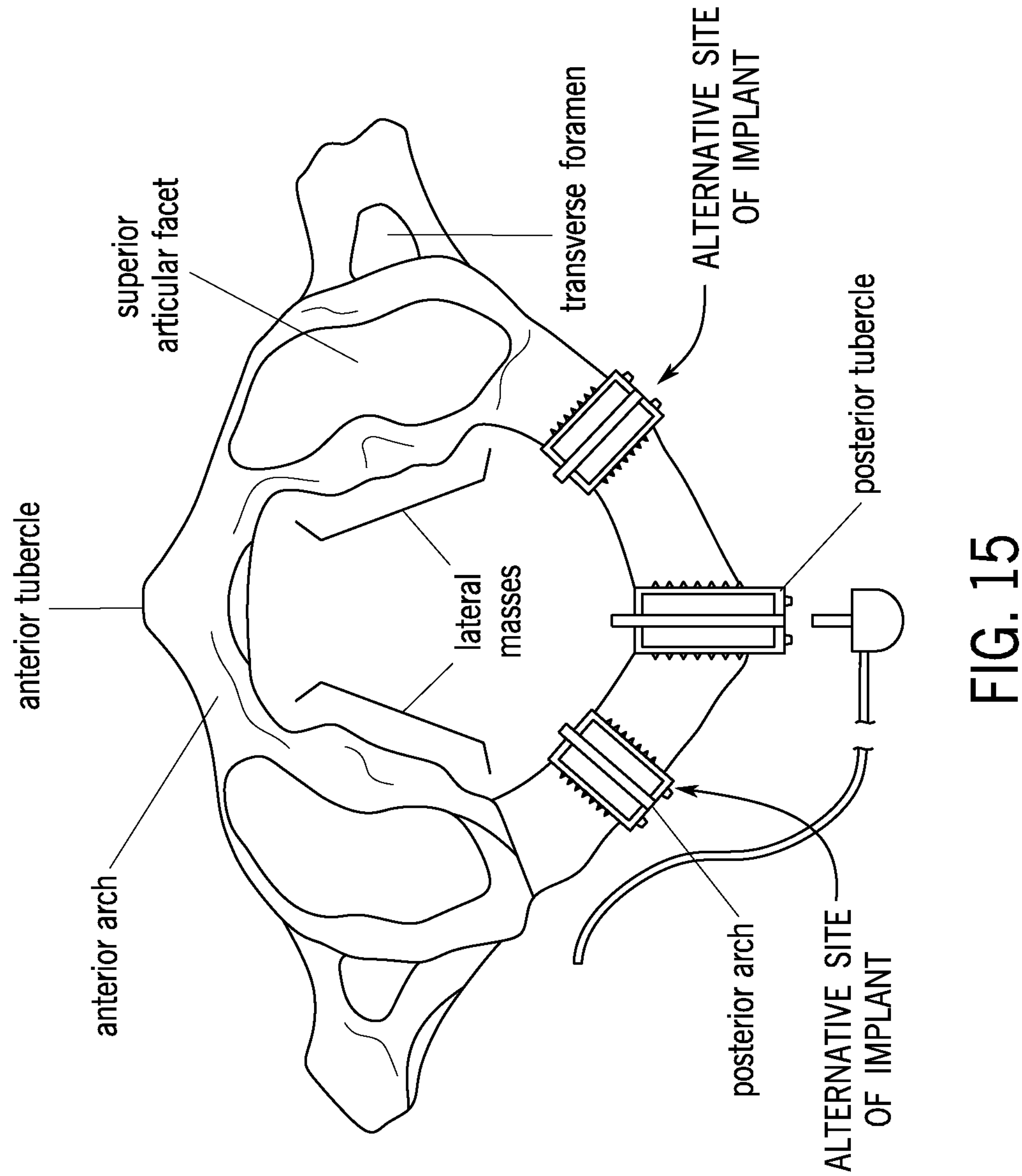
FIG. 15 shows a schematic illustration of different implant locations for the implants described herein.

FIG. 15 shows a schematic illustration of different possible implant locations for the implants described herein. For example, as shown in FIG. 15, the bone that receives an implant can be the C1 vertebrae at the posterior arch. As a more specific example, a hole can be drilled at a location on the posterior arch at the posterior tubercle of the C1 vertebrae, a location on the posterior arch of the C1 vertebrae between the posterior tubercle and the superior articular facet, or a location on the posterior arch of the C1 vertebrae between the posterior tubercle and the anterior articular facet. Then, the implant can be implanted in the hole. In some cases, prior to creating a hole in the bone, the bone can be shaved flat (e.g., with a bone blade).

Figure 16:
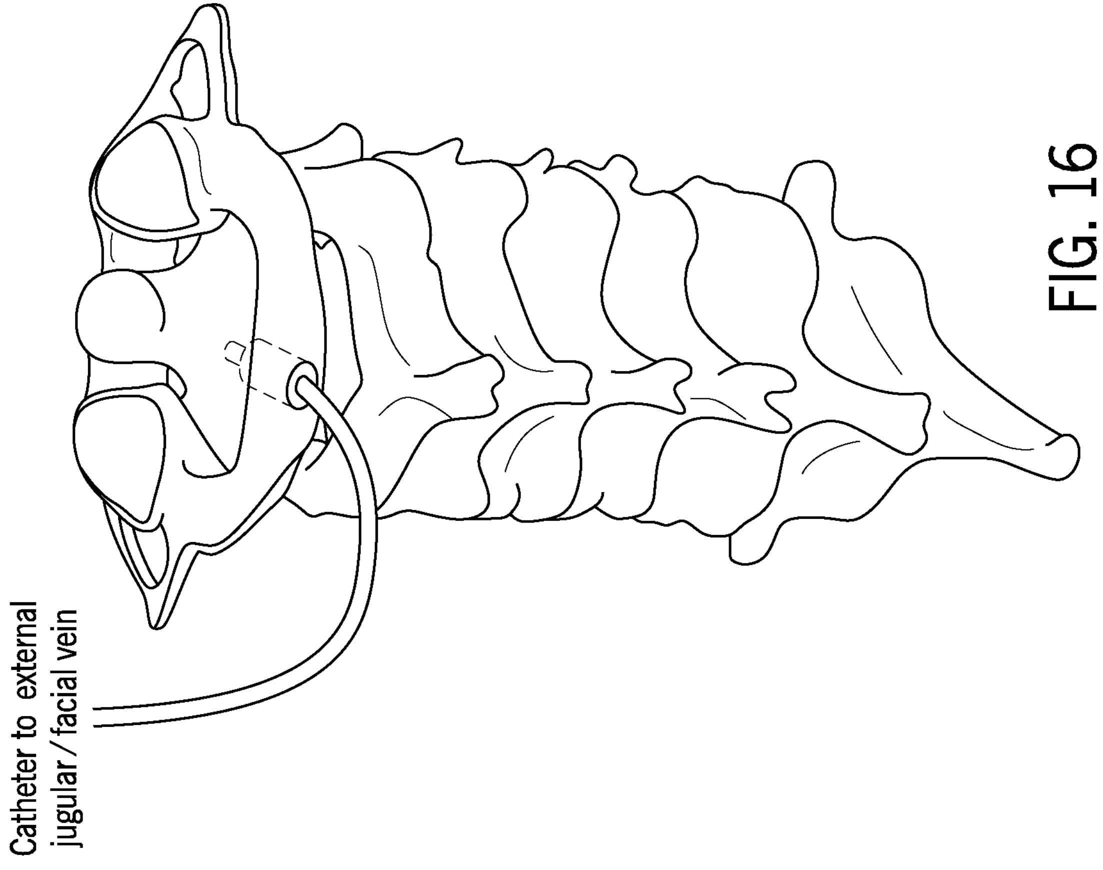
FIG. 16 shows a schematic illustration of an implant location of an implant described herein.

FIG. 16 shows a schematic illustration of an implant location of an implant described herein. In some configurations, the implant location of the implant and the implant location of a plug described herein (e.g., at a blood vessel) can be coplanar. For example, the implant and the plug can reside in the same axial plane (e.g., when implanted). In this way, the CSF can drain more naturally, for example, as the head is oriented differently and the CSF pressure changes.

The present disclosure has described one or more preferred embodiments. However, it should be appreciated that many equivalents, alternatives, variations, and modifications, aside from those expressly stated, are possible and within the scope of the invention.

It is to be understood that the disclosure is not limited in its application to the details of construction and the arrangement of components set forth in the accompanying description or illustrated in the accompanying drawings. The disclosure is capable of other embodiments and of being practiced or carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

As used herein, unless otherwise limited or defined, discussion of particular directions is provided by example only regarding particular embodiments or relevant illustrations. For example, discussion of "top," "front," or "back" features is generally intended as a description only of the orientation of such features relative to a reference frame of a particular example or illustration. Correspondingly, for example, a "top" feature may sometimes be disposed below a "bottom" feature (and so on), in some arrangements or embodiments. Further, references to particular rotational or other movements (e.g., counterclockwise rotation) are generally intended to describe only movement relative to a reference frame of a particular example of illustration.

According to the disclosure, certain operations of methods or systems executing those methods may be represented schematically in the figures or otherwise discussed herein. Unless otherwise specified or limited, representation in the figures of particular operations in a particular spatial order may not necessarily require those operations to be executed in a particular sequence corresponding to the particular spatial order. Correspondingly, certain operations represented in the figures, or otherwise disclosed herein, can be executed in different orders than are expressly illustrated or described, as appropriate for particular embodiments of the disclosure. Further, certain operations can be executed in parallel in some embodiments, including by dedicated parallel processing devices or separate computing devices configured to interoperate as part of a large system.

As used herein in the context of computer implementation, unless otherwise specified or limited, the terms "component," "system," "module," and the like are intended to encompass part or all of computer-related systems that include hardware, software, a combination of hardware and software, or software in execution. For example, a component may be, but is not limited to being, a processor device, a process being executed (or executable) by a processor device, an object, an executable, a thread of execution, a computer program, or a computer. By way of illustration, both an application running on a computer and the computer can be a component. One or more components (or system, module, and so on) may reside within a process or thread of execution, may be localized on one computer, may be distributed between two or more computers or other processor devices, or may be included within another component (or system, module, and so on).

In some implementations, devices or systems disclosed herein can be utilized or installed using methods embodying aspects of the disclosure. Correspondingly, the description herein of particular features, capabilities or intended purposes of a device or system is generally intended to inherently include disclosure of a method of using such features for the intended purposes, a method of implementing such capabilities, and a method of installing disclosed (or otherwise known) components to support these purposes or capabilities. Similarly, unless otherwise indicated or limited, the discussion herein of any method of manufacturing or using a particular device or system, including installing the device or system, is intended to inherently include disclosure, as embodiments of the disclosure, of the utilized features and implemented capabilities of such device or system.

As used herein, unless otherwise defined or limited, ordinal numbers are used herein for convenience of reference-based generally on the order in which particular components are presented for the relevant part of the disclosure. In this regard, for example, designations such as "first," "second," etc., generally indicate only the order in which the relevant component is introduced for discussion and generally do not indicate or require a particular spatial arrangement, functional or structural primacy or order.

As used herein, unless otherwise defined or limited, directional terms are used for the convenience of reference for discussion of particular figures or examples. For example, references to downward (or other) directions or top (or other) positions may be used to discuss aspects of a particular example or figure but do not necessarily require similar orientation or geometry in all installations or configurations.

This discussion is presented to enable a person skilled in the art to make and use embodiments of the disclosure. Various modifications to the illustrated examples will be readily apparent to those skilled in the art, and the generic principles herein can be applied to other examples and applications without departing from the principles disclosed herein. Thus, embodiments of the disclosure are not intended to be limited to embodiments shown but are accorded the widest scope consistent with the principles and features disclosed herein and the claims below. The accompanying detailed description is to be read with reference to the figures, in which like elements in different figures have like reference numerals. The figures, which are not necessarily to scale, depict selected examples and are not intended to limit the scope of the disclosure. Skilled artisans will recognize the examples provided herein have many useful alternatives and fall within the scope of the disclosure.

The disclosure's various features and advantages are set forth in the following claims.

What is claimed is:

1. An implant method for accessing cerebrospinal fluid (CSF) within the subarachnoid space surrounding the spinal cord, comprising: creating an opening in a bone of a vertebral lamina using a drill bit, the drill bit being configured to create the opening without advancing into the spinal cord; driving a first body of an implant into the opening in a bone to place the implant into the bone, thereby securing the implant to the bone, the opening in the bone including a shelf at a distal end thereof including a hole therein, the implant configured for insertion into the vertebral lamina and anchoring therein, the implant comprising the first body defining a first end and a second end opposite the first end, the first body including an exterior surface including threads, the implant further comprising an extension that extends past the second end of the first body, the extension having a narrower diameter than the second end of the first body, a needle removably coupled to the first body and extending past the second end of the first body, the first body being configured to be driven into the opening in the bone adjacent to the shelf such that the extension protrudes through the hole in the shelf of the bone, and the extension having a length configured to protrude through the hole in the shelf of the bone without piercing a central nervous system tissue adjacent to the bone; and piercing, with the needle by driving the first body into the opening in the bone, the central nervous system tissue adjacent to the bone thereby placing an end of the needle into an anatomical cavity to drain fluid from the anatomical cavity through the needle; and inserting a plug into an opening in a blood vessel, the plug including: a second body, a mechanical stop coupled to the second body, a bore directed entirely through the second body, and a retainer having an opening, the second body configured to be received through the opening to secure the retainer to the second body, and wherein upon inserting the plug into the opening in the blood vessel, a wall of the blood vessel is positioned between the mechanical stop and the retainer, and wherein the fluid from the anatomical cavity drains through the bore of the second body into the blood vessel.

2. The implant method of claim 1, further comprising a bore directed through the first body, wherein the method further comprises:

removably inserting the needle through the bore so that a portion of the needle extends past the second end of the first body.

3. The implant method of claim 2, wherein the needle does not have a lumen.

4. The implant method of claim 2, wherein the bore is a first bore, wherein the implant further comprises an insert having a second bore directed entirely through the insert, wherein the method further comprises:

inserting the insert through the first bore of the first body so that a portion of the insert extends past the second end of the first body, and coupling the insert to the first body when the insert is placed into the first bore of the first body.

5. The implant method of claim 4, wherein the central nervous system tissue is the dura mater, wherein the anatomical cavity is the cisterna magna, and wherein the method further comprises: piercing the dura mater using the needle to form an opening in the dura mater, and retreating the needle from the opening in the dura mater such that the portion of the insert that extends past the second end of the first body is inserted through the opening, thereby bringing the second bore of the insert in fluid communication with the cisterna magna.

6. The implant method of claim 1, wherein the central nervous system tissue is the dura mater, wherein the anatomical cavity is the cisterna magna, wherein the needle includes a lumen, and wherein the method further comprises: advancing the needle to enter the cisterna magna so that the lumen of the needle is brought into fluid communication with the cisterna magna such that cerebrospinal fluid flows through the needle.

7. The implant method of claim 1, further comprising:

advancing the needle to extend past the second end of the first body a predetermined distance that is less than 3 millimeters.

8. The implant method of claim 1, further comprising a tool interface positioned at the first end of the first body, wherein the method further comprises:

engaging the tool interface using a socket of a ratchet to drive rotation of the first body of the implant into the bone.

9. The implant method of claim 1, further comprising a reservoir including a first port in fluid communication with the reservoir and a second port in fluid communication with the reservoir, wherein the method further comprises:

coupling the reservoir to the implant to bring the first port into fluid communication with a bore of the implant.

10. The implant method of claim 9, wherein the first port is substantially perpendicular to the second port.

11. The implant method of claim 1, wherein the mechanical stop extends beyond the opening in the blood vessel and contacts the wall of the blood vessel, wherein the opening of the retainer is configured to be smaller than a portion of the second body, and wherein the method further comprises:

inserting the portion of the second body into the opening of the retainer such that the opening expands and the retainer retracts around the portion of the second body to secure the retainer to the second body.

12. The implant method of claim 1, wherein the mechanical stop is configured to be compressed into a compressed state and expanded into an expanded state, wherein the method further comprises:

inserting the mechanical stop in the compressed state through the opening of the blood vessel, wherein the mechanical stop transitions from the compressed state to the expanded state while the mechanical stop is positioned in the blood vessel, and wherein the mechanical stop in the expanded state is blocked from being retreated back through the opening of the blood vessel.

13. The implant method of claim 1, wherein a first location of the opening in the bone and a second location of the opening in the blood vessel are coplanar.

14. The implant method of claim 1, wherein the implant further includes:

a bore that is directed through the body and the extension, wherein the method further comprises:

extending the needle through the bore and past the extension.

* * * * *